United States Patent
Meyer et al.

(10) Patent No.: US 10,548,494 B2
(45) Date of Patent: Feb. 4, 2020

(54) METHOD FOR DETERMINING A PERSONALIZED CARDIAC MODEL USING A MAGNETIC RESONANCE IMAGING SEQUENCE

(71) Applicants: UNIVERSITE DE LORRAINE, Nancy (FR); CENTRE HOSPITALIER REGIONAL DE NANCY, Nancy (FR)

(72) Inventors: Christophe Meyer, Nancy (FR); Pierre-André Vuissoz, Villers les Nancy (FR); Laurent Bonnemains, Diarville (FR); Jacques Felblinger, Mereville (FR)

(73) Assignees: UNIVERSITE DE LORRAINE, Nancy (FR); CENTRE HOSPITALIER REGIONAL DE NANCY, Nancy (FR)

( * ) Notice: Subject to any disclaimer, the term of this patent is extended or adjusted under 35 U.S.C. 154(b) by 798 days.

(21) Appl. No.: 15/109,382

(22) PCT Filed: Jan. 7, 2014

(86) PCT No.: PCT/IB2014/000076
§ 371 (c)(1),
(2) Date: Jun. 30, 2016

(87) PCT Pub. No.: WO2015/104571
PCT Pub. Date: Jul. 16, 2015

(65) Prior Publication Data
US 2016/0324427 A1 Nov. 10, 2016

(51) Int. Cl.
*A61B 5/026* (2006.01)
*A61B 5/055* (2006.01)
(Continued)

(52) U.S. Cl.
CPC ............ *A61B 5/0263* (2013.01); *A61B 5/055* (2013.01); *A61B 5/7285* (2013.01);
(Continued)

(58) Field of Classification Search
CPC ..... A61B 5/0263; A61B 5/055; A61B 5/7285; G01R 33/5673; G01R 33/5676;
(Continued)

(56) References Cited

U.S. PATENT DOCUMENTS

2002/0032376 A1* 3/2002 Miyazaki ............. A61B 5/0263
                                                           600/410
2004/0267147 A1* 12/2004 Sullivan ................. A61B 5/024
                                                           600/528
(Continued)

OTHER PUBLICATIONS

Markl et al.; 4D Flow MRI; Journal of Magnetic Resonance Imaging 36:1015-1036 (2012); published on Oct. 22, 2012 (Year: 2012).*

(Continued)

*Primary Examiner* — Amanda Lauritzen Moher
*Assistant Examiner* — Chao Sheng
(74) *Attorney, Agent, or Firm* — Greer, Burns & Crain, Ltd.

(57) ABSTRACT

A method is provided for determining a personalized cardiac model, including steps of (i) computing a velocity time profile of a blood flow across a selected area of the heart or the aorta during at least one cardiac cycle, using data acquired with a Magnetic Resonance Imaging (MRI) device; (ii) performing a segmentation of the velocity time profile so as to identify cardiac phases according to a predefined generic cardiac model; and (iii) computing normalized time location and/or duration of the cardiac phases within cardiac cycles so as to define a personalized cardiac model.

13 Claims, 5 Drawing Sheets

(51) Int. Cl.
*G01R 33/567* (2006.01)
*A61B 5/00* (2006.01)
*G01R 33/563* (2006.01)

(52) U.S. Cl.
CPC ..... *G01R 33/5673* (2013.01); *G01R 33/5676* (2013.01); *G01R 33/563* (2013.01); *G01R 33/56308* (2013.01); *G01R 33/56316* (2013.01); *G01R 33/56325* (2013.01)

(58) Field of Classification Search
CPC ............ G01R 33/56316; G01R 33/563; G01R 33/56308; G01R 33/56325
See application file for complete search history.

(56) References Cited

U.S. PATENT DOCUMENTS

| | | | |
|---|---|---|---|
| 2006/0100503 | A1 | 5/2006 | Takai et al. |
| 2006/0161060 | A1* | 7/2006 | Pai ................... G01R 33/563 600/431 |
| 2008/0054900 | A1* | 3/2008 | Polzin .............. G01R 33/56308 324/309 |
| 2010/0041982 | A1* | 2/2010 | Kitane ................. A61B 5/055 600/419 |
| 2013/0088227 | A1* | 4/2013 | Wernik ............... A61B 5/0263 324/309 |
| 2015/0327783 | A1* | 11/2015 | Wang ................. A61B 5/0263 600/419 |
| 2015/0374237 | A1* | 12/2015 | Hu ....................... A61B 5/055 600/413 |

OTHER PUBLICATIONS

Gatehouse et al.; Flow measurement by cardiovascular magnetic resonance: a multi-centre multi-vendor study of background phase offset errors that can compromise the accuracy of derived regurgitant or shunt flow measurements; Journal of Cardiovascular Magnetic Resonance; 201012:5; p. 1-8 (Year: 2010).*

Wong et al.; Cardiac Flow Analysis Applied to Phase Contrast Magnetic Resonance Imaging of the Heart; Annals of Biomedical Engineering; Aug. 2009, vol. 37, Issue 8, pp. 1495-1515; online published on May 23, 2009 (Year: 2009).*

Yu et al.; Quantification of the Pulse Wave Velocity of the Descending Aorta Using Axial Velocity Profiles From Phase-Contrast Magnetic Resonance Imaging; Magnetic Resonance in Medicine; vol. 56, Issue 4, pp. 876-883; published on Aug. 31, 2006 (Year: 2006).*

Feinstein et al., "Using Cardiac Phase to Order Reconstruction (CAPTOR): A Method to Improve Diastolic Images," JMRI (1997), 7(5), pp. 794-798.

Pelc et al., "Phase Contrast Cine Magnetic Resonance Imaging," Magnetic Resonance Quarterly (1991), 7(4), pp. 229-254.

Vembar et al., "A dynamic approach to identifying desired physiological phases for cardiac imaging using multislice spiral CT," Medical Physics (2003), 30(7), pp. 1683-1693.

International Search Report from International Patent Application No. PCT/IB2014/000076, dated Jul. 11, 2014.

* cited by examiner (a)  (b)

METHOD FOR DETERMINING A PERSONALIZED CARDIAC MODEL USING A MAGNETIC RESONANCE IMAGING SEQUENCE

BACKGROUND

The invention relates to a method for determining a personalized cardiac model using a magnetic resonance imaging sequence.

The field of the invention is, but not limited to, the imaging of the heart with Magnetic Resonance Imaging (MRI) techniques.

The movement of the heart is relatively periodic and can be understood as the repetition of cardiac cycles. However, within a cardiac cycle, this movement is quite complex and physiologists have defined several cardiac phases. Depending on the level of precision wanted, the cardiac cycle may be divided into different numbers of phases.

The simplest division is systole for contraction vs. diastole for relaxation. However, systole may also be divided into isovolumic contraction (before opening of the output valve) and ejection (after opening of the output valve). In a similar way, diastole may be divided in at least five phases: isovolumic relaxation, early ventricular filling, diastasis, auricular ejection, auriculoventricular delay.

The division of cardiac cycles into a given number of phases and the prediction of the duration of these phases when heart rate changes from beat to beat is called "cardiac model".

Magnetic Resonance Imaging (MRI) techniques are very efficient techniques for the functional exploration of the heart. But they are facing the problem that the acquisition of the data is made slice by slice in a time-consuming process. Without specific precautions, the images of a moving organ such as the heart may be blurred. So imaging methods have been developed, which use the periodical nature of the heart beat to synchronize the acquisitions.

Cardiac Magnetic Resonance (CMR) imaging is based either on cine acquisition (producing a video with several frames of a mean cardiac cycle) which is considered the gold-standard to quantify left ventricle volume, ventricle mass and stroke volume, or on acquisition of static images which are very useful to characterize myocardial tissue and to detect for example oedema or fibrosis.

In both cases, CMR requires a cardiac model (the knowledge of the durations of each cardiac phases), either to determine a cardiac "rest" period in which data can be acquired with minimal motion (for cardiac triggered types of acquisition like black blood, T1 and T2 maps, Late Gadolinium Enhancement, coronaries, etc.) or to attribute acquired k-space lines to cardiac phases in retrospective reconstruction of cine acquisitions. This is especially important for high temporal resolution cine acquisitions.

However, the known cardiac models are not patient-adaptive.

The currently published cardiac model used in the context of cine MRI is a linear stretching of the systole and diastole periods separately. Although this model seems to be the most recent one and is used routinely and worldwide for cine reconstructions, it is based on data acquired 45 years ago with a technology now considered obsolete. In this study, a linear fit on inter-individual values was performed within a cohort of subjects. This model predicts the mean duration of systole and diastole within a general population. However, this model was not designed to predict variations within different cardiac cycles of a single subject. It cannot cope with physiological differences among subjects due for example to pathological conditions, diurnal variation in the systolic intervals, pressure changes or medication that alter systolic or diastolic times.

It is for instance known that equations from males and females differ slightly, and that the left ventricular ejection duration increases independently from heart rate from infancy to puberty and is prolonged in the elderly.

It is an object of the invention to provide a method for the construction of a personalized cardiac model adapted to each subject.

It is also an object of the invention to provide a method for the construction of a personalized cardiac model whose parameters are adjusted to meet the particular patient's cardiac cycles instead of using generic and fixed parameters extracted from a whole cohort.

It is also an object of the invention to provide a method for the construction of a personalized cardiac model which allows improving the prediction of the rest time period where imaging should be done for triggered MRI sequences.

It is also an object of the invention to provide a method for the construction of a personalized cardiac model which allows improving the time resolution precision in MRI cine retrospective reconstructions.

SUMMARY

Such objects are accomplished through a method for determining a personalized cardiac model, characterized in that it comprises steps of:
- computing a velocity time profile of a blood flow across a selected area of the heart or the aorta during at least one cardiac cycle, using data acquired with a Magnetic Resonance Imaging (MRI) device,
- performing a segmentation of said velocity time profile so as to identify cardiac phases according to a predefined generic cardiac model,
- computing a time location and/or a duration of said cardiac phases within cardiac cycles so as to define a personalized cardiac model.

The method of the invention may further comprise a step of acquisition and processing of a Real-Time Phase Contrast (RTPC) signal sequence in a scan plane with a spatial orientation normal to a direction of flow of the blood, said RTPC sequence being based on a phase contrast MRI sequence where only the central k-space line is acquired.

The RTPC sequence may use a frequency encoding direction with an orientation chosen so as to project velocity fields from different sources to areas as distinct as possible along the frequency encoding axis.

The acquisition and processing of the Real-Time Phase Contrast (RTPC) signal sequence may be done in one of the following configurations:
- in a quasi axial scan plane cross-sectioning the ascending aorta with a frequency encoding direction going through the ascending and descending aorta cross-sections;
- in an intra-cardiac short-axis scan plane with a frequency encoding direction going through inferolateral and anteroseptal cardiac segments.

The method of the invention may further comprise a recording of an ElectroCardioGram (ECG) signal, said ECG signal being used for triggering the Magnetic Resonance Imaging (MRI) acquisitions.

The method of the invention may further comprise a step of computing a 1D+t velocity map with one spatial axis and one time axis, by applying to the RTPC signal sequence unidimensional Fourier transforms along the frequency encoding direction;

The method of the invention may further comprise a step of identifying a region of the 1D+t velocity map in which the velocity time profile is representative of the cardiac phases.

It may further comprise the steps of:
carrying out a Singular Value Decomposition (SVD) on the 1D+t velocity map;
with a threshold algorithm applied on the spatial weighting returned by the SVD, identifying in the 1D+t velocity map a set of regions of interest (ROI) of contiguous pixels for one or several of the first principal components issued from the SVD decomposition;
computing a spatial average value of the velocity time profile in the ROIs;
identifying the ROI with the spatial average value having the highest power in the cardiac spectral band around the heart beat rate;
computing the velocity time profile by using the spatial average value of the ROI having the largest size along the spatial dimension axis among all ROIs having more than 40% of said highest power.

The method of the invention may further comprise steps of:
computing a baseline of the velocity time profile representative of a null blood flow velocity;
for at least one cardiac cycle, (i) detecting the peak with the highest velocity corresponding to the systolic cardiac phase by fitting with a pre-defined curve shape, and (ii) identifying its time location and/or its duration within said cardiac cycle by locating the times of crossing of the baseline by the velocity time profile curve around said peak.

The baseline may be computed iteratively using the following steps:
computing a baseline by applying a low-pass filter with a cut-off frequency close to the heart beat rate to the velocity time profile;
using histogram analysis and application of a threshold, generating a new velocity time profile by setting extreme or most distant values of the velocity time profile relative to the baseline to the baseline value.

According to some modes of realization, the method of the invention may further comprise steps of, for at least one cardiac cycle:
detecting the peak with the highest velocity among the still non-identified peaks by fitting with a pre-defined curve shape, and matching it with a cardiac phase using the generic cardiac model;
identifying its time location and/or its duration within said cardiac cycle by locating the times of crossing of the baseline by the velocity time profile curve around said peak.

The method of the invention may further comprise a step of computing a curve fitting the time location and/or the duration of the identified cardiac phases to the cardiac cycle duration, so as to generate the personalized cardiac model.

According to another aspect, it is proposed a medical imaging method, comprising steps of:
determining a personalized cardiac model by using the method of the invention;
acquiring medical imaging data of the heart using said personalized cardiac model for taking into account the cardiac phases.

According to some modes of implementation, it is proposed a MRI medical imaging method, which comprises a step of triggering a MRI sequence using the personalized cardiac model.

According to some other modes of implementation, it is proposed a MRI medical imaging method, which comprises steps of:
asynchronous acquisition of MRI data;
reconstruction of a high temporal resolution Cine MRI sequence using the personalized cardiac model.

So, according to the invention, the cardiac model parameters are adjusted to meet the particular patient's cardiac cycles instead of using generic and fixed parameters extracted from a whole cohort.

By assessing cardiac phases durations in a number of cardiac cycles of various lengths from the same subject with an automatic method, thus measuring the variability of subject-specific cardiac phases duration, a personalized cardiac model is built.

A velocity curve representative of the blood flow or tissue motion in a selected area is obtained with a high temporal resolution and in real-time using a Magnetic Resonance Imaging (MRI) technique.

The velocity curve is used to detect and measure the cardiac phases separately during several heartbeats for a subject.

This allowed the creation of an adaptive cardiac model able to better predict the cardiac phases compared to non patient-specific cardiac models.

This model can then be used directly, for instance, in the triggering and the reconstruction of a later MRI exam.

BRIEF DESCRIPTION OF THE DRAWINGS

The methods according to embodiments of the present invention may be better understood with reference to the drawings, which are given for illustrative purposes only and are not meant to be limiting. Other aspects, goals and advantages of the invention shall be apparent from the descriptions given hereunder.

DETAILED DESCRIPTION

Figure 1:
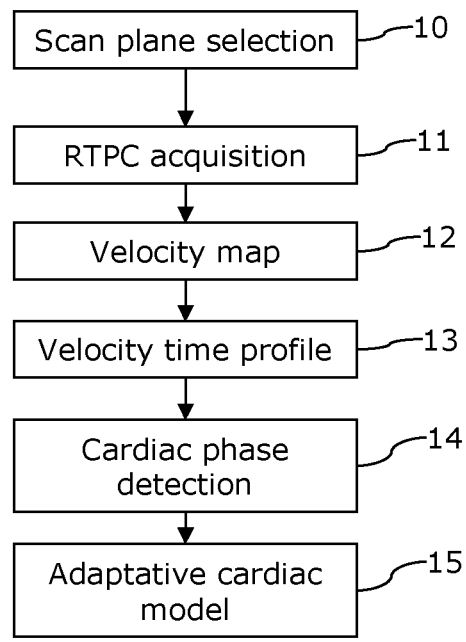
FIG. 1 shows a flow chart of the method of the invention.

With reference to FIG. 1, we will now describe a mode of implementation of the invention which allows the construction of a personalized cardiac model adapted to each subject undergoing Cardiac Magnetic Resonance (CMR).

The method of the invention comprises a first step 10 of selection of a slice or a scan plane to be used to calibrate the model.

There for, a Cardiac MRI is performed. It can be done for instance using a 3 T Signa HDxt scanner from General Electric®, Waukesha, Wis., with subjects in supine position and using an eight-element cardiac phased-array coil.

Localizing scans are recorded, and a slice or a scan plane usable for the calibration is located.

The choice of the scan plane depends on the kind of cardiac model which is to be used. For instance:
- a scan plane located at the aorta may be used to obtain a cardiac model with N=2 cardiac phases (systole/diastole);
- an intra-cardiac short axis scan plane may be used to obtain a cardiac model with up to N=7 cardiac phases (isovolumic contraction, ejection, isovolumic relaxation, early atrial filling, diastasis, atrial filling and atrioventricular delay).

The method of the invention further comprises a step 11 of acquisition of a Real-Time Phase Contrast (RTPC) signal in the chosen slice, normal to the direction of velocity of the blood flow.

The RTPC sequence is based on a bidimensional (2D) phase contrast MRI sequence, where only the central k-space line is acquired, similarly to the RACE sequence. One-directional through-slice interleaved velocity encoding is used. The velocity is measured successively in two opposite directions for each line of the k-space. The final value of the velocity is obtained by computing a difference between successive measurements in opposite directions.

The acquisition may be done for instance with the following MRI scan parameters:
Field Of View (FOV): 350 mm;
Slice thickness: 8 mm;
Flip angle: 15 degrees;
Bandwidth: 62.5 KHz;
Acquisition matrix (M×P): 256×1;
Repetition time (TR): 6.6 ms
Echo time (TE): 3.4 ms;
Encoding velocity (Venc): 50 cm/s;
Excitations repetitions: 1;
k-Lines per segment: 1;
Temporal resolution: 6.6 ms;
Typical scan duration: 100 s.

With these parameters, the temporal resolution for RTPC acquisitions is 6.6 ms.

The orientation of the frequency encoding direction is chosen so as to project different velocity fields from different sources to separate areas on the frequency line, along the frequency encoding direction (at least as much as possible, some overlap may sometimes be unavoidable).

The scan planes may comprise for instance:
- a quasi axial scan plane cross-sectioning the ascending aorta with a frequency direction going through the two aorta cross-sections (ascending and descending aorta);
- a scan plane in a so-called "short axis" with a frequency direction going through inferolateral and anteroseptal cardiac segments. The "short axis" corresponds to specific heart cross section orientations, in which both ventricles are visible.

The RTPC acquisition is performed during several heartbeats (for instance 128 heartbeats) and during varying heart rates (for instance using natural heart rate variation during free-breathing).

ElectroCardioGram (ECG) is recorded and used for triggering the MRI.

Cardiac cycles for which an obvious error in QRS detection on the ECG occurs are discarded from the analysis (i.e. for instance cycles with instantaneous heart rate below 30 or above 120 beats per minute).

The method of the invention further comprises a step 12 of computing of a velocity map.

The RTPC data is transformed into a 1D+t image space by applying a unidimensional (1D) Fourier transform along the frequency encoding direction.

The 1D+t image space is an image space with one coordinate being a dimension (1D, for instance in pixels), and one coordinate being the time (t).

To limit noisy air regions and reduce processing time, only the central part corresponding to about 50% of the field of view (FOV) is kept, while checking that the organ of interest is included.

For each of the MRI receiving coils, the 1D+t phase dataset is unwrapped using a fast bidimensional (2D) phase unwrapping algorithm. A velocity map is then computed by subtraction of data relative to consecutive echoes of the interleaved acquisitions. A temporal resolution equal to TR is obtained by computing the forward and the backward differences.

Finally, a global 1D+t velocity map is computed, which corresponds to a magnitude-weighted sum of the respective coil's velocity maps.

Figure 2:
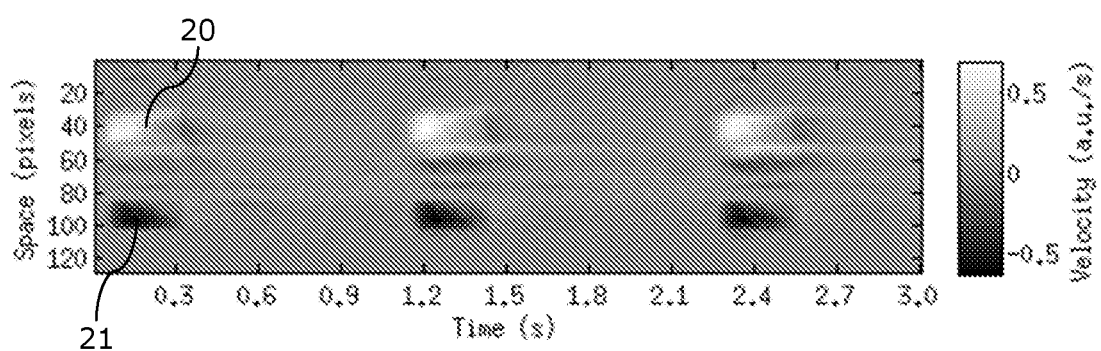
FIG. 2 shows a velocity map corresponding to a scan plane located on the aorta.

FIG. 2 shows an example of velocity map corresponding to a scan plane located on the aorta, which is suitable for determining a cardiac model with N=2 cardiac phases (systole/diastole).

One axis corresponds to the time of acquisition. Three cardiac cycles (out of 128) are represented.

The other axis corresponds to the spatial direction of the slice perpendicular to the direction of projection of the velocity field across the slice. So, one velocity profile is represented for each acquisition time.

Positive velocity (in bright areas 20) and negative velocity (in dark areas 21) correspond respectively to systolic blood flow in the ascending and descending aorta.

Similarly, FIG. 3b shows an example of velocity map corresponding to an intra-cardiac short-axis scan plane, which is suitable for determining a cardiac model with N=6 cardiac phases. One second of RTPC signal containing one cardiac cycle (out of 128) is represented.

The intra-cardiac short-axis scan plane 30 from which the velocity map is computed is shown on FIG. 3a.

The method of the invention further comprises a step 13 of computation of a velocity time profile.

An automatic spatial segmentation of the 1D+t velocity map is performed in order to determine the area in which the velocity time profile is the most representative of the cardiac cycles.

A Singular Value Decomposition (SVD) is carried out on the 1D+t velocity map.

Figure 4:
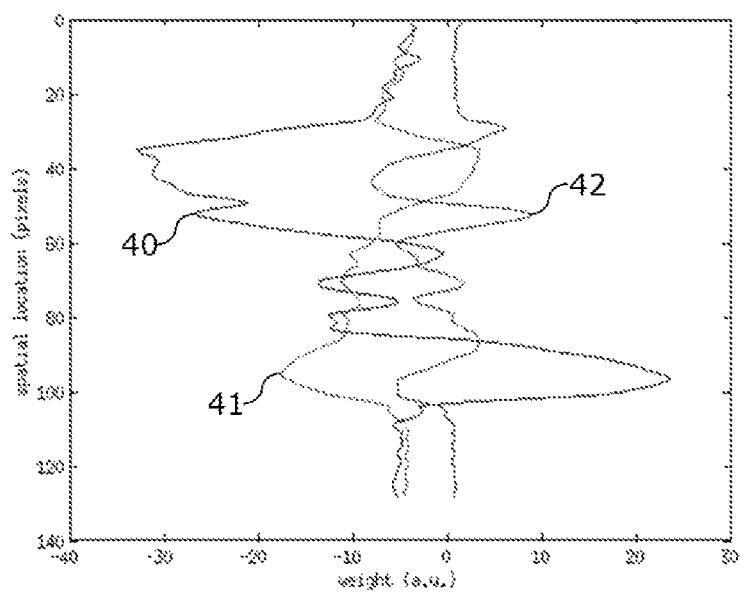
FIG. 4 shows the spatial weights of the three first modes of the SVD of the velocity map of FIG. 2, in the aorta.

FIG. 4 shows the spatial weights of the three first modes of the SVD of the velocity map of FIG. 2, corresponding to the aorta. More precisely, it shows the spatial weight of the first mode 40, the spatial weight of the second mode 41 and the spatial weight of the third mode 42.

The spatial weights of the modes are represented in function of the same spatial dimension (or direction) as the velocity map.

A threshold algorithm using the spatial weighting returned by the SVD is applied to the velocity map in order to generate a set of spatial locations, corresponding to a set of regions of interest (ROI) of contiguous pixels, for each of the first three principal components issued from the SVD decomposition.

For each ROI, the time course (of time profile) of the mean velocity in the ROI is computed. The ROI with the velocity time course having the highest power in the cardiac spectral band (using the mean heart rate+/−0.03 Hz) is determined, and used to select all ROIs having more than 40% of this maximum. Among those selected ROIs, the ROI 31 having the largest size in pixels (or spatial unit) is chosen.

That ROI 31 is shown on FIG. 3b for the intra-cardiac short-axis scan plane case.

Finally, the velocity is computed for each acquisition time by cumulating or averaging the corresponding velocity values of the pixels of the selected ROI.

As a result, a velocity time profile is obtained. In the current example it is 128 cardiac cycles long.

Figure 5:
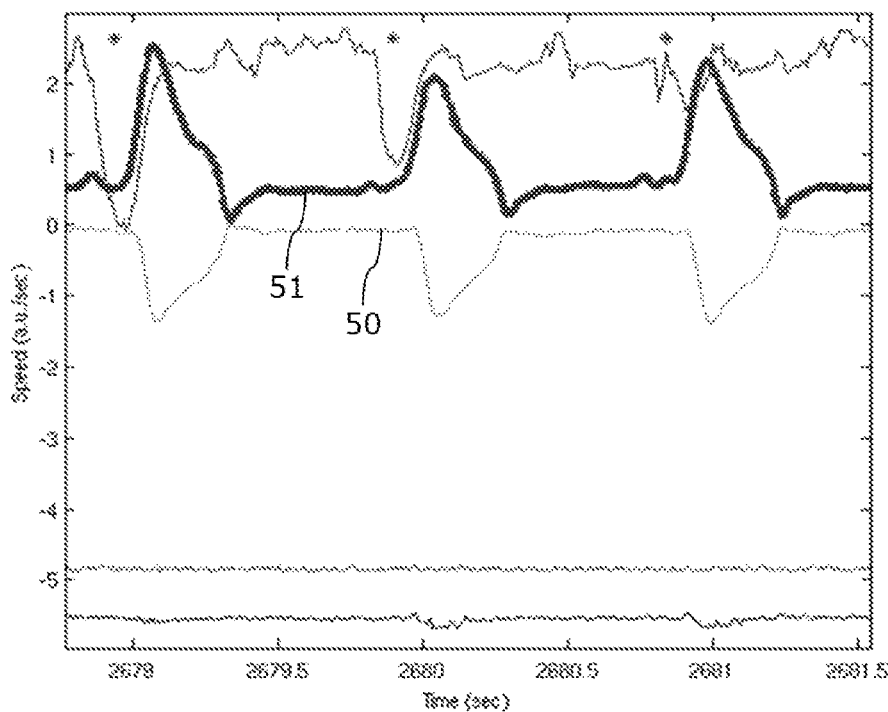
FIG. 5 shows a small portion of velocity time profiles extracted from several possible ROIs in the velocity map of FIG. 2.

FIG. 5 shows an example of velocity time profiles 50 extracted from several candidate ROIs of a velocity map corresponding to the aorta (FIG. 2). The selected velocity time profile 51 is the one automatically chosen by the algorithm, corresponding to the ROI having the largest size.

In the aorta scan plane (corresponding to FIG. 2 and FIG. 5), the velocity time profile can be interpreted as the consequence of the ejected ascending aortic blood flow because, physiologically, ascending aorta is the location of highest variations of velocity in the chosen slice. The absolute values of velocity are not considered because they derive from the summation of all velocities along the phase encoding direction (as only the central k-space line is obtained). However, the duration of the highest peak of velocity (called S-wave) is considered as a measure of systole duration. So, only two phases (N=2) may be detected, namely the systole and the diastole.

In the intra-cardiac short-axis scan plane location (corresponding to FIG. 3), the velocity time profile can be interpreted as the velocity of blood inside the heart during its phases, and so N=6 cardiac phases may be detected.

Figure 6:
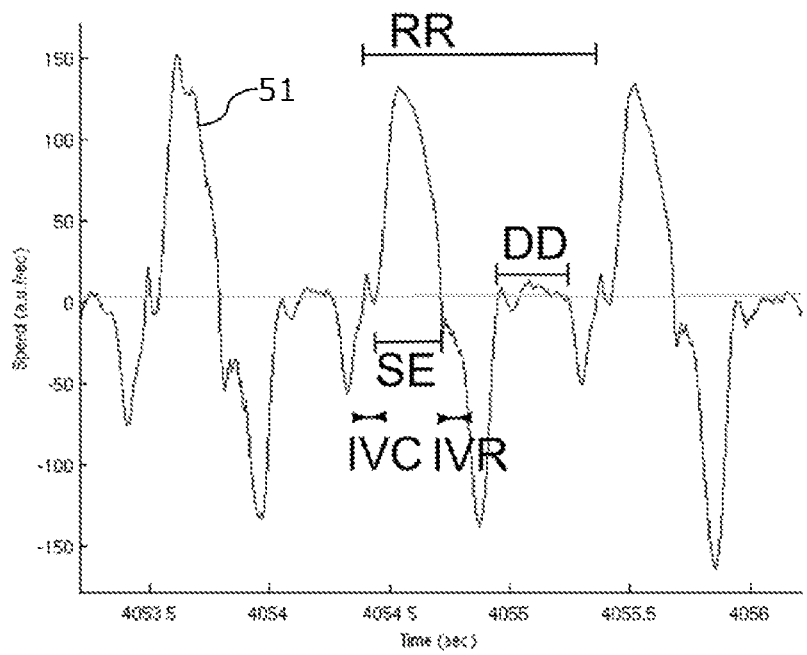
FIG. 6 shows a velocity curve obtained in intra-cardiac short-axis scan plane.

FIG. 6 shows an example of velocity time profile obtained in intra-cardiac short-axis scan plane. Cardiac phases are shown, with the cardiac cycle (RR), the IsoVolumic Contraction (IVC), the Systolic Ejection (SE), the IsoVolumic Relaxation (IVR) and the Diastolic Diastasis (DD).

The method of the invention further comprises a step 14 of detection of the cardiac phases, by processing the selected velocity curve 51.

Figure 7:
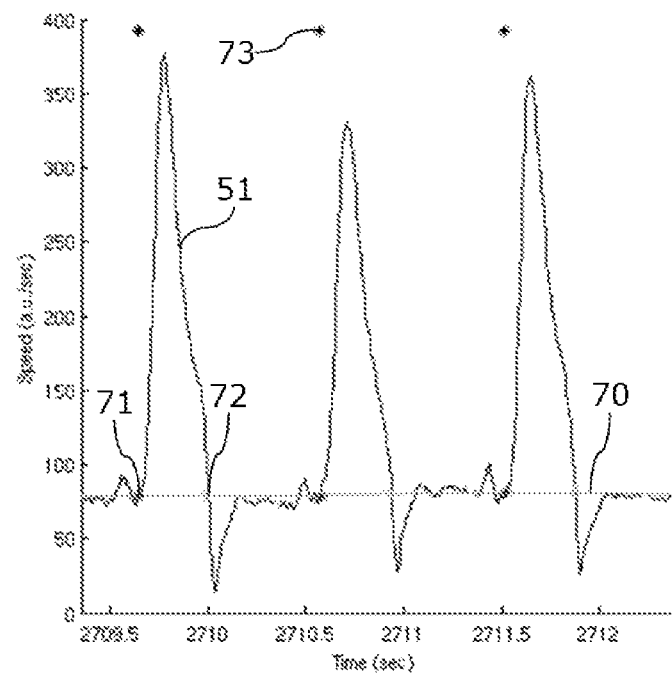
FIG. 7 shows portion of the velocity time profile obtained in aorta scan plane with overlaid R-wave detected on ECG, start of ejection and end of ejection.

With reference to FIG. 7, systolic waves (S-waves) are automatically detected on the velocity curve 51 by detecting the peaks with the maximum velocity, with a shape fitted to a parabola (second order polynomial).

The start time 71 and the end time 72 of forward systolic velocity, defined by the S-wave crossing a baseline 70, are recorded.

The baseline 70 is computed iteratively as follows:
a current baseline is computed by applying a low-pass filter with a cut-off frequency of 0.35 Hz, close to the heart beat rate, to the current velocity curve;
then, using histogram analysis and application of a threshold, a new velocity curve is generated by setting extreme or most distant values of the current velocity curve relative to the current baseline to the baseline value.
The new velocity curve is then used as current velocity curve in the next iteration;
at each further iteration, the threshold for extreme values is lowered.

The duration of systole is computed, as illustrated in FIG. 7, by measuring the delay between the ECG triggering (R-wave 73) and the end of forward systolic velocity 72. The online R-wave detection is post-processed in order to reposition the detection at the top of the QRS complex of ECG lead I.

When systole duration is not plausible (for instance with values below 100 ms or above 500 ms), the corresponding cardiac cycle is discarded.

The invention is not limited to N=2 cardiac phases.

Figure 3:
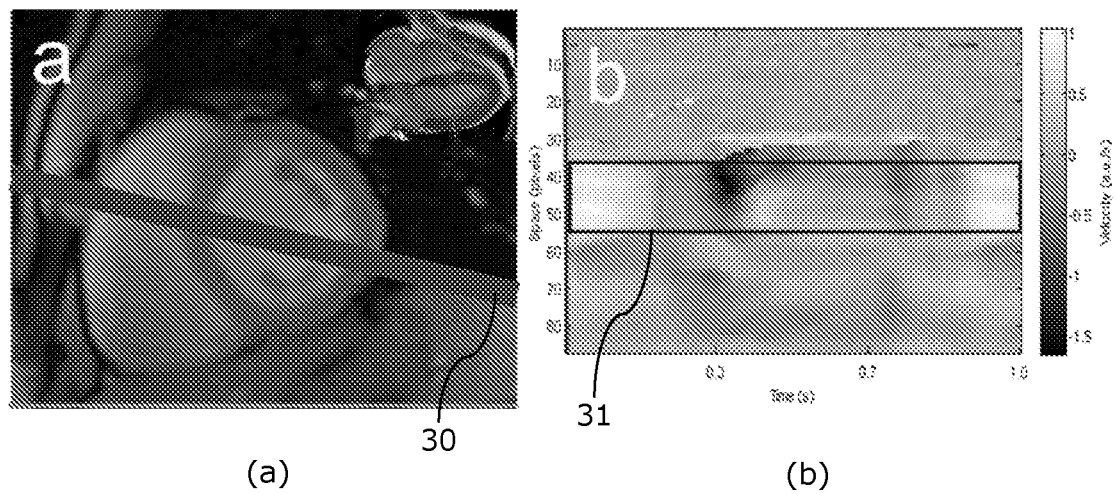
FIG. 3 shows (a) an intra-cardiac short-axis scan plane, and (b) a corresponding velocity map.
Figure 8:
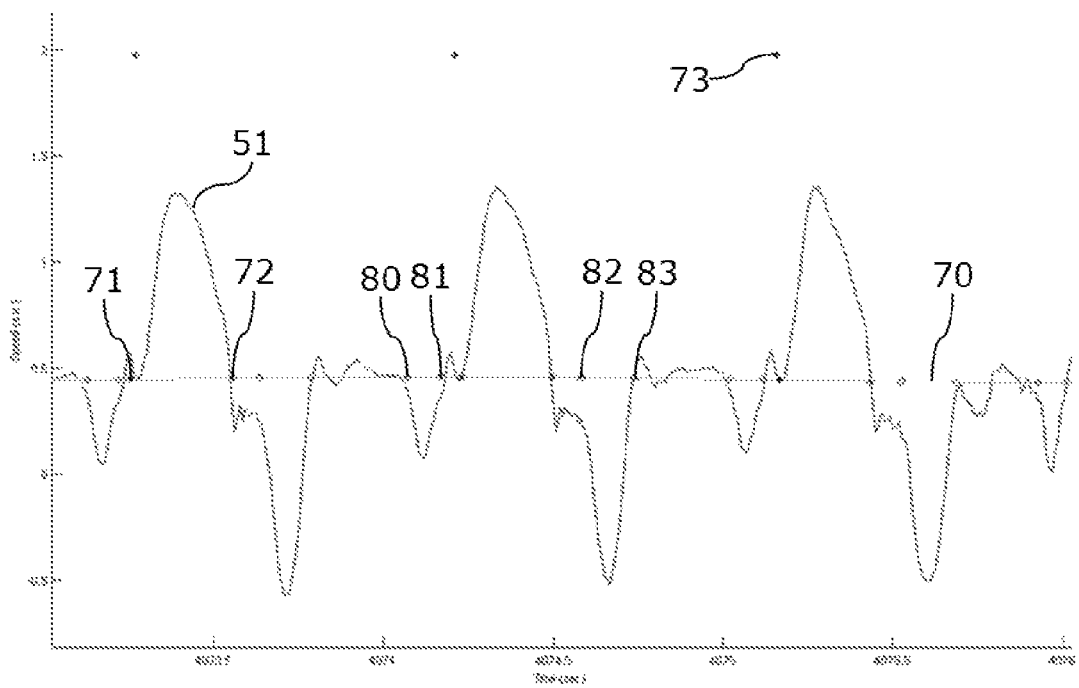
FIG. 8 shows portion of the velocity time profile obtained in intra-cardiac short-axis scan plane with overlaid R-wave detected on ECG and detection of: start of ejection, end of ejection, start of early filling, end of early filling, start of atrial filling and end of atrial filling.

With reference to FIG. 8, when velocity containing distinct waves related to cardiac motion can be measured (using for instance intra-cardiac short-axis scan plane as shown in FIG. 3 and FIG. 6), the invention can also calibrate these waves in function of heart rate.

Other waves (than systolic waves) are automatically detected on the velocity curve by iteratively detecting the peaks with the next maximum velocity, with a shape fitted to a parabola (second order polynomial).

The start time and the end time of each peak, defined by the corresponding wave crossing the baseline 70, are recorded.

The duration of the peaks and/or the gaps between the peaks (corresponding to the cardiac phases) is then computed by measuring the delay between the start time and the end time of these peaks or gaps.

FIG. 8 illustrates shows portion of the velocity time profile 51 obtained in intra-cardiac short-axis scan plane, with overlaid R-wave 73 detected on ECG and detection of: start of ejection 71, end of ejection 72, start of early filling 82, end of early filling 83, start of atrial filling 80 and end of atrial filling 81 defined by baseline 70 crossings of second order polynomial fitting the peaks.

In the intra-cardiac short-axis scan plane, six cardiac phases can be thus be computed (three waves: S, E, A and their gaps).

The method of the invention further comprises a step 15 of definition of a personalized, Patient-Adaptive Cardiac Model.

The cardiac phase durations are computed for each valid cardiac cycle as previously explained. Their respective duration (and/or their time location within the heart beat cycle) is then matched or fitted to the heart beat rate. Preferably, a first order (linear) law is used for the curve fitting.

So, we obtain a personalized Patient-Adaptive Cardiac Model which consists in a linear model expressing wave peaks duration as a function of heart rate. As the model is derived from measurements made on the patient, it fits for each subject separately.

Figure 9:
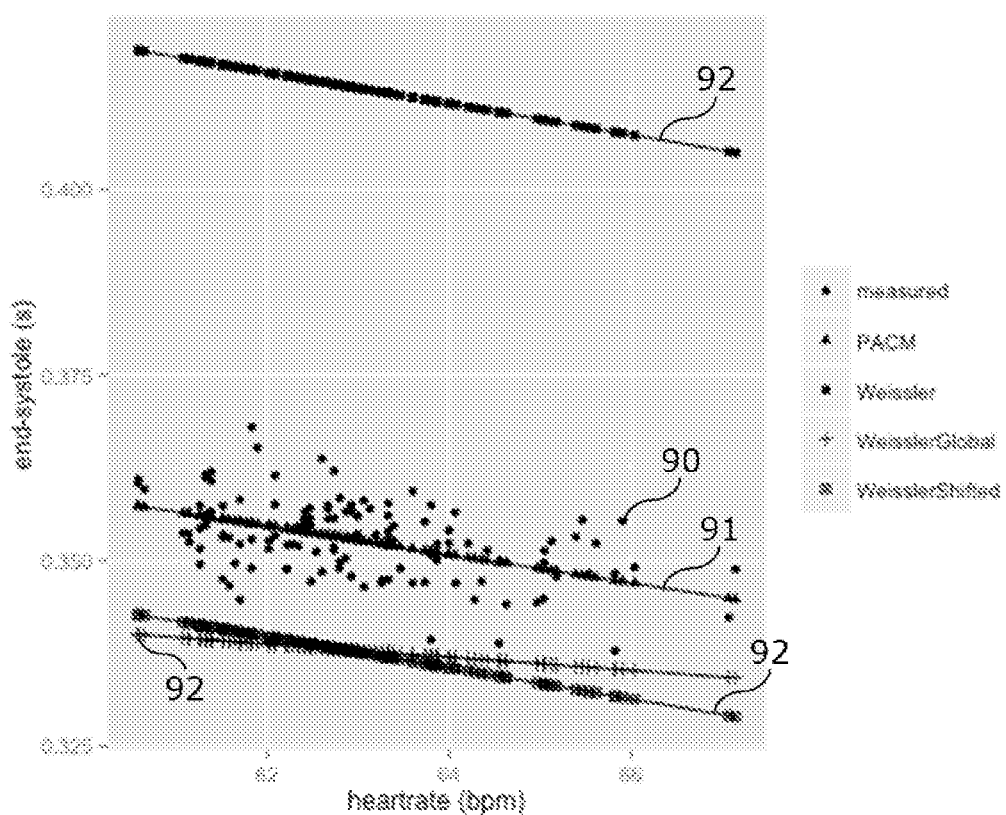
FIG. 9 shows measurements of end-systolic time for one person, and corresponding end-systolic time predicted by the model of the invention and models of the prior art.

FIG. 9 shows examples of measurements of end-systolic time for one volunteer in function of the heart rate. The measurements are made using an aortic scan plane.

The plot shows the individual measurements 90, the values 91 predicted by the Patient-Adaptive Cardiac Model of the invention, and values 92 predicted by three models of the prior art (Weissler, Weissler global and Weissler shifted).

As it can be seen, the Patient-Adaptive Cardiac Model of the invention predicts the end systole time more reliably than all other tested models.

It should be noted that in the model of the invention both the calibration and the error in prediction are dependent upon the temporal resolution of the calibration acquisition. Of course the higher the temporal resolution, the better (in the described mode of realization we achieved 6.6 ms temporal resolution).

We will now describe possible use or implementation of the adaptative cardiac model of the invention. Of course, these examples are in no way limitative.

According to a mode of implementation, the adaptative cardiac model of the invention may be used to trigger a MRI sequence.

In a first step, the model is calibrated for the patient as described previously.

Then, the calibrated cardiac model is used as a drop-in replacement for the global cardiac model used in the adaptive black blood triggered sequence.

So, advantageously, the trigger delay of the acquisition window is adapted to the specificity of the patient. Also, the duration of the acquisition window can be adapted because the length of the cardiac phase is known.

As a result, the acquisition stays more consistently in the prescribed cardiac phase (systole or diastasis) and the image quality is improved (less mixing of cardiac phases).

According to another mode of implementation, the adaptative cardiac model of the invention may be used for the reconstruction of a high temporal resolution Cine MRI sequence.

In a first step, the model is calibrated for the patient as described previously.

Then, the calibrated cardiac model is used as a drop-in replacement for the global cardiac model used in the reconstruction of free-breathing asynchronous balanced-ssfp sequence in the Cine-GRICS algorithm.

As a result, the distribution of asynchronously acquired k-space lines into cardiac phase bins (images) is more correct regarding the real cardiac phases of the patient. The image quality is improved (less mixing of cardiac phases).

Generally speaking, when using MRI imaging modalities, the cardiac model of the invention may be calibrated in a preliminary step with the MRI device, and then used in the measurement sequence. In recurrent exams however, the model may be calibrated once for a patient and then used in several measurement sequences.

A model calibrated for a patient using a MRI device may of course be used with any other relevant imaging modality, such as computed tomography (CT) or untrasounds.

While this invention has been described in conjunction with a number of embodiments, it is evident that many alternatives, modifications and variations would be or are apparent to those of ordinary skill in the applicable arts. Accordingly, it is intended to embrace all such alternatives, modifications, equivalents and variations that are within the spirit and scope of this invention.

The invention claimed is:

1. A method for determining a personalized cardiac model, comprising steps of:
    computing a velocity time profile of a blood flow across a selected area of the heart or the aorta during at least one cardiac cycle, using data acquired with a Magnetic Resonance Imaging (MRI) device;
    performing a segmentation of said velocity time profile so as to identify cardiac phases according to a predefined generic cardiac model;
    computing at least one of a time location or a duration of said cardiac phases within cardiac cycles so as to define a personalized cardiac model;
    acquiring and processing a Real-Time Phase Contrast (RTPC) signal sequence in a scan plane with a spatial orientation normal to a direction of flow of the blood, said RTPC sequence being based on a phase contrast MRI sequence where only the central k-space line is acquired;
    computing a 1D+t velocity map with one spatial axis and one time axis, by applying to the RTPC signal sequence unidimensional Fourier transforms along the frequency encoding direction;
    carrying out a Singular Value Decomposition (SVD) on the 1D+t velocity map; and
    with a threshold algorithm applied on the spatial weighting returned by the SVD, identifying in the 1D+t velocity map a set of regions of interest (ROI) of contiguous pixels for one or several of the first principal components issued from the SVD decomposition.

2. The method of claim 1, which further comprises a recording of an ElectroCardioGram (ECG) signal, said ECG signal being used for triggering the Magnetic Resonance Imaging (MRI) acquisitions.

3. The method of claim 1, which further comprises a step of identifying a region of the 1D+t velocity map in which the velocity time profile is representative of the cardiac phases.

4. The method of claim 1, which further comprises steps of:
    computing a spatial average value of the velocity time profile in the ROIs;
    identifying the ROI with the spatial average value having the highest power in the cardiac spectral band around the heart beat rate; and
    computing the velocity time profile by using the spatial average value of the ROI having the largest size along the spatial dimension axis among all ROIs having more than 40% of said highest power.

5. The method of claim 1, wherein the RTPC sequence uses a frequency encoding direction with an orientation chosen so as to project velocity fields from different sources to areas as distinct as possible along the frequency encoding axis.

6. The method of claim 5, wherein the acquisition and processing of the Real-Time Phase Contrast (RTPC) signal sequence is done in one of the following configurations:
    in a quasi axial scan plane cross-sectioning the ascending aorta with a frequency encoding direction going through the ascending and descending aorta cross-sections;
    in an intra-cardiac short-axis scan plane with a frequency encoding direction going through inferolateral and anteroseptal cardiac segments.

7. The method of claim 1, which further comprises steps of:
    computing a baseline of the velocity time profile representative of a null blood flow velocity; and
    for at least one cardiac cycle, (i) detecting a peak with the highest velocity corresponding to the systolic cardiac phase by fitting with a pre-defined curve shape, and (ii) identifying at least one of its time location or its duration within said cardiac cycle by locating the times of crossing of the baseline by the velocity time profile curve around said peak.

8. The method of claim 7, wherein the baseline is computed iteratively using the following steps:
    computing a baseline by applying a low-pass filter with a cut-off frequency of 0.35 Hz to the velocity time profile; and
    using histogram analysis and application of a threshold, generating a new velocity time profile by setting extreme or most distant values of the velocity time profile relative to the baseline to the baseline value.

9. The method of claim 7, which further comprises steps of, for at least one cardiac cycle:

detecting the peak with the highest velocity among the still non-identified peaks by fitting with a pre-defined curve shape, and matching it with a cardiac phase using the generic cardiac model; and identifying at least one of its time location or its duration within said cardiac cycle by locating the times of crossing of the baseline by the velocity time profile curve around said peak.

10. The method of claim 7, which further comprises a step of computing a curve fitting at least one of the time location or the duration of the identified cardiac phases to the cardiac cycle duration, so as to generate the personalized cardiac model.

11. A medical imaging method, comprising steps of:
determining a personalized cardiac model by using the method of claim 1; and
acquiring medical imaging data of the heart using said personalized cardiac model for taking into account the cardiac phases.

12. The MRI medical imaging method according to claim 11, which comprises a step of triggering a MRI sequence using the personalized cardiac model.

13. The MRI medical imaging method according to claim 11, which comprises steps of:
asynchronous acquisition of MRI data; and
reconstruction of a temporal resolution Cine MRI sequence using the personalized cardiac model.

\* \* \* \* \*